(12) United States Patent
La et al.

(10) Patent No.: US 10,920,213 B2
(45) Date of Patent: Feb. 16, 2021

(54) HEAT-RESISTANT CARBONIC ANHYDRASE MUTANTS AND COMPOSITION FOR CAPTURING CARBON DIOXIDE CONTAINING THE SAME

(71) Applicant: SK Innovation Co., Ltd., Seoul (KR)

(72) Inventors: Yeon Hwa La, Daejeon (KR); Tae Wan Kim, Daejeon (KR); Jae Yang Song, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 34 days.

(21) Appl. No.: 16/525,935

(22) Filed: Jul. 30, 2019

(65) Prior Publication Data

US 2020/0040324 A1    Feb. 6, 2020

(30) Foreign Application Priority Data

Aug. 2, 2018    (KR) .................. 10-2018-0090236

(51) Int. Cl.
*C12N 9/88*    (2006.01)
*C12N 15/52*   (2006.01)
*F25J 3/02*    (2006.01)
*C12N 15/70*   (2006.01)

(52) U.S. Cl.
CPC ............... *C12N 9/88* (2013.01); *C12N 15/52* (2013.01); *C12N 15/70* (2013.01); *F25J 3/0266* (2013.01); *C12Y 402/01001* (2013.01)

(58) Field of Classification Search
None
See application file for complete search history.

(56) References Cited

U.S. PATENT DOCUMENTS

| | | |
|---|---|---|
| 6,232,117 B1 | 5/2001 | Mather |
| 8,697,428 B2 | 4/2014 | Borchert et al. |
| 2016/0222371 A1 | 8/2016 | Cha et al. |
| 2019/0241881 A1 | 8/2019 | Salmon et al. |

FOREIGN PATENT DOCUMENTS

| | | |
|---|---|---|
| EP | 0307247 A2 | 3/1989 |
| KR | 20160098652 | 3/2019 |
| WO | 9108291 A2 | 6/1991 |
| WO | 2008095057 A2 | 8/2008 |
| WO | 2018017792 A1 | 1/2018 |

OTHER PUBLICATIONS

Kawarabayasi et al.; "Complete Genome Sequence of an Aerobic Thermoacidophilic Crenarchaeon, Sulfolobus tokodaii strain7"; DNA Research; Jan. 1, 2001; pp. 123-140; vol. 8; XP055636027.

"Carbonic anhydrase [Metallosphaera yellowstonensis]—Protein—NCBI"; ; http://www.ncbi.nlm.nih.gov/protein/WP_009072641 (retrieved on Oct. 25, 2019); National Center for Biotechnology Information; May 28, 2013; XP055636013.

"Lsan_2877—Carbonic anhydrase—Legionella santicrucis—Lsan_2877 gene & protein"; http://www.uniprot.org/uniprot/A0A0W0YID9 (retrieved on Oct. 25, 2019); Uniprot; Mar. 16, 2016; XP055636019.

"TQ35_04350—Carbonic anhydrase—Candidatus Aramenus sulfurataquae—TQ35_04350 gene & protein"; www.uniprot.org/uniprot/A0A0F2LR90 (retrieved on Oct. 25, 2019); Uniprot; Apr. 6, 2016.

Di Fiore et al., "Thermostable Carbonic Anhydrases in Biotechnological Applications", International Journal of Molecular Sciences, 2015, pp. 15456-15480, vol. 16.

Puxty et al., "Carbon Dioxide Postcombustion Capture: A Novel Screening Study of the Carbon Dioxide Absorption Performance of 76 Amines", Environmental Science & Technology, 2009, pp. 6427-6433, vol. 43, No. 16.

Veawab et al., "Corrosion Behavior of Carbon Steel in the CO2 Absorption Process Using Aqueous Amine Solutions", Industrial & Engineering Chemistry Research, 1999, pp. 3917-3924, vol. 38.

*Primary Examiner* — Suzanne M Noakes
(74) *Attorney, Agent, or Firm* — The Webb Law Firm (57) ABSTRACT

Disclosed are a carbonic anhydrase mutant having heat resistance at a high temperature of 80° C. as well as excellent activity to capture carbon dioxide and a composition for capturing carbon dioxide containing the same. The heat-resistant carbonic anhydrase mutant can be applied to a high-temperature carbon dioxide capture process due to high stability at high temperatures and a high carbon dioxide hydration rate.

12 Claims, 5 Drawing Sheets

Specification includes a Sequence Listing.

SEQUENCE LISTING

<160> NUMBER OF SEQ ID NOS: 7

<210> SEQ ID NO 1
<211> LENGTH: 187
<212> TYPE: PRT
<213> ORGANISM: Sulfolobales archaeon AZ1

<400> SEQUENCE: 1

```
Met Arg Val Ile Met Ser Cys Met Asp Tyr Arg Leu Thr Glu Glu Ile
1               5                   10                  15

Met Lys Lys Met Asp Gln Asn Thr Ile Val Leu Arg Asn Ala Gly Ala
            20                  25                  30

Asn Val Asn Glu Phe Lys Asp Ile Leu Lys Ser Leu Asn Pro Asp Glu
        35                  40                  45

Val Val Tyr Leu Pro His Thr Asp Cys Ala Ala Met Lys Leu Val Leu
    50                  55                  60

Ser Ser Val Lys Gln Gly Glu Gln Val Thr Pro Lys Ile Glu Ser Ser
65                  70                  75                  80

Leu Val Ser Gln Phe Arg Gly Arg Gln Phe Asn Asp Leu Lys Glu Leu
                85                  90                  95

Glu Glu Leu Asn Leu Lys Leu Gly Leu Glu Thr Ile Lys Gln Val Val
            100                 105                 110

Pro Lys Ala Lys Val Ile Ser Glu Leu Ile Asp Val Asn Lys Leu Lys
        115                 120                 125

Trp Pro Glu Arg Lys Pro Val Val Tyr Leu Leu Lys Ser Thr Ser Lys
    130                 135                 140

Tyr Thr Asn Glu Met Ile Gly Gly Tyr Val Ile Gln Ser Met Asn Lys
145                 150                 155                 160

Thr Ser Ile Glu Ala Asp Leu Glu Ile Ala Ser Lys Leu Asn Leu Lys
                165                 170                 175

Val Val Lys Asp Glu Phe Ser Asn Ala Arg Asp
            180                 185
```

<210> SEQ ID NO 2
<211> LENGTH: 187
<212> TYPE: PRT
<213> ORGANISM: Artificial Sequence
<220> FEATURE:
<223> OTHER INFORMATION: Variant 1.0

<400> SEQUENCE: 2

```
Met Arg Val Ile Met Ser Cys Met Asp Tyr Arg Leu Thr Glu Glu Ile
1               5                   10                  15

Met Lys Lys Met Asp Gln Asn Thr Ile Val Leu Arg Asn Ala Gly Ala
            20                  25                  30

Asn Val Asn Glu Phe Lys Asp Ile Leu Lys Ser Leu Asn Pro Asp Glu
        35                  40                  45

Val Val Tyr Leu Pro His Thr Asp Cys Ala Ala Met Lys Leu Val Leu
```

```
                50                  55                  60
Ser Ser Val Lys Gln Gly Glu Gln Val Thr Pro Lys Ile Glu Ser Ser
 65                  70                  75                  80

Leu Val Ser Gln Phe Arg Gly Arg Gln Phe Asn Asp Leu Lys Glu Leu
                 85                  90                  95

Glu Glu Leu Asn Leu Lys Leu Gly Leu Glu Thr Ile Lys Gln Val Val
                100                 105                 110

Pro Lys Ala Lys Val Ile Ser Glu Leu Ile Asp Val Asn Lys Leu Lys
                115                 120                 125

Trp Pro Glu Arg Lys Pro Val Val Tyr Leu Leu Lys Ser Thr Ser Lys
                130                 135                 140

Tyr Thr Asn Glu Met Ile Gly Gly Tyr Val Ile Gln Ser Met Asn Lys
145                 150                 155                 160

Thr Ser Ile Glu Ala Asp Leu Gly Ile Ala Ser Lys Leu Asn Leu Lys
                165                 170                 175

Val Val Lys Asp Glu Phe Ser Asn Ala Arg Asp
                180                 185

<210> SEQ ID NO 3
<211> LENGTH: 187
<212> TYPE: PRT
<213> ORGANISM: Artificial Sequence
<220> FEATURE:
<223> OTHER INFORMATION: Variant 13.0

<400> SEQUENCE: 3

Met Arg Val Ile Met Ser Cys Met Asp Tyr Arg Leu Thr Glu Glu Ile
  1               5                  10                  15

Met Lys Lys Met Asp Gln Asn Thr Ile Val Leu Arg Asn Ala Gly Ala
                 20                  25                  30

Asn Val Asn Glu Phe Lys Asp Ile Leu Lys Ser Leu Asn Pro Asp Glu
                 35                  40                  45

Val Val Tyr Leu Gly His Thr Asp Cys Gly Ala Met Lys Leu Val Leu
                 50                  55                  60

Ser Ser Val Lys Gln Gly Glu Gln Val Thr Pro Lys Ile Glu Ser Ser
 65                  70                  75                  80

Leu Val Ser Gln Phe Arg Gly Arg Gln Phe Asn Asp Leu Lys Glu Leu
                 85                  90                  95

Glu Glu Leu Asn Leu Lys Leu Gly Leu Glu Thr Ile Lys Gln Val Val
                100                 105                 110

Pro Lys Ala Lys Val Ile Ser Glu Leu Ile Asp Val Asn Lys Leu Lys
                115                 120                 125

Trp Pro Glu Arg Lys Pro Val Val Tyr Leu Leu Lys Ser Thr Ser Lys
                130                 135                 140

Tyr Thr Asn Glu Met Ile Gly Gly Tyr Val Ile Gln Ser Met Asn Lys
145                 150                 155                 160

Thr Ser Ile Glu Ala Asp Leu Gly Ile Ala Ser Lys Leu Asn Leu Lys
                165                 170                 175

Val Val Lys Asp Glu Phe Ser Asn Ala Arg Asp
                180                 185

<210> SEQ ID NO 4
<211> LENGTH: 27
<212> TYPE: DNA
<213> ORGANISM: Artificial Sequence
<220> FEATURE:
<223> OTHER INFORMATION: wild-type primer
```

```
<400> SEQUENCE: 4
cacaccgact gcggcgcgat gaaactg                                       27

<210> SEQ ID NO 5
<211> LENGTH: 27
<212> TYPE: DNA
<213> ORGANISM: Artificial Sequence
<220> FEATURE:
<223> OTHER INFORMATION: wild-type primer

<400> SEQUENCE: 5
cagtttcatc gcgccgcagt cggtgtg                                       27

<210> SEQ ID NO 6
<211> LENGTH: 26
<212> TYPE: DNA
<213> ORGANISM: Artificial Sequence
<220> FEATURE:
<223> OTHER INFORMATION: mutant primer

<400> SEQUENCE: 6
gttgtgtacc tgggccacac cgactg                                        26

<210> SEQ ID NO 7
<211> LENGTH: 26
<212> TYPE: DNA
<213> ORGANISM: Artificial Sequence
<220> FEATURE:
<223> OTHER INFORMATION: mutant primer

<400> SEQUENCE: 7
cagtcggtgt ggcccaggta cacaac                                        26
```

HEAT-RESISTANT CARBONIC ANHYDRASE MUTANTS AND COMPOSITION FOR CAPTURING CARBON DIOXIDE CONTAINING THE SAME

CROSS-REFERENCE TO RELATED APPLICATION

This application claims priority to Korean Patent Application No. 10-2018-0090236 filed Aug. 2, 2018, the disclosure of which is hereby incorporated by reference in its entirety. The Sequence Listing associated with this application is filed in electronic format via EFS-Web and is hereby incorporated by reference into the specification in its entirety. The name of the text file containing the Sequence Listing is 1904821_ST25.txt. The size of the text file is 6,1360 bytes, and the text file was created on Jul. 9, 2019.

TECHNICAL FIELD

The present invention relates to a heat-resistant carbonic anhydrase mutant and a composition for capturing carbon dioxide containing the same. More particularly, the present invention relates to a carbonic anhydrase mutant having heat resistance at a high temperature of 80° C. and excellent activity to capture carbon dioxide, and a composition for capturing carbon dioxide containing the same.

BACKGROUND ART

A carbonic anhydrase is a metalloenzyme containing zinc ions, which rapidly accelerates the hydration of carbon dioxide. As depicted below, the carbonic anhydrase nucleophilically reacts with carbon dioxide to produce bicarbonate and then greatly facilitates the formation of bicarbonate through exchange with water (G. Puxty et. al. Environ. Sci. Technol. 43:6427, 2009; A. Veawab et. al. Ind. Eng. Chem. Res. 38:3917, 1999).

The carbonic anhydrase accelerates the reaction up to 10 million times faster than a natural reaction, but has problems of lowered productivity upon practical application to a real-world process and the requirement to improve enzyme stability at a high regeneration tower temperature.

Therefore, there is an urgent demand for developing a carbonic anhydrase that has stability at 80° C. or higher, which is applicable to an actual regeneration tower, rather than a carbonic anhydrase having heat resistance at about 40 to 60° C., which is generally used in the field to which the present invention pertains.

Accordingly, the present inventors have made intensive efforts to develop a carbonic anhydrase maintaining excellent activity to capture carbon dioxide at a high temperature of 80° C. or higher for a long time. As a result, the present inventors have constructed a *Sulfolobales archaeon* AZ1-derived KJR78985.1 protein mutant and have found that the mutant maintained a high carbon dioxide capture activity at a high temperature of 80° C. or higher for a long period of time. Based on this finding, the present invention has been completed.

DISCLOSURE

Technical Problem

Therefore, it is one object of the present invention to provide a carbonic anhydrase mutant capable of maintaining a high carbon dioxide capture activity at a high temperature of 80° C. or higher for a long period of time.

It is another object of the present invention to provide a composition for capturing carbon dioxide containing the carbonic anhydrase mutant.

Technical Solution

In accordance with one aspect of the present invention, provided is a carbonic anhydrase mutant including an A58G mutation in an amino acid sequence set forth in SEQ ID NO: 1.

In accordance with another aspect of the present invention, provided are a nucleic acid encoding the carbonic anhydrase mutant, a recombinant vector including the nucleic acid, and a recombinant microorganism introduced with the recombinant vector.

In accordance with another aspect of the present invention, provided is a method for producing a carbonic anhydrase mutant including: (a) culturing the recombinant microorganism to produce a carbonic anhydrase mutant; and (b) recovering the produced carbonic anhydrase mutant.

In accordance with another aspect of the present invention, provided is a composition for capturing carbon dioxide containing the carbonic anhydrase mutant.

In accordance with another aspect of the present invention, provided is a method for capturing carbon dioxide at 40 to 90° C. using the carbonic anhydrase mutant.

Advantageous Effects

The heat-resistant carbonic anhydrase mutant according to the present invention has high stability as well as a fast carbon dioxide hydration rate at high temperatures, and thus can be applied to a high-temperature carbon dioxide capture process.

BEST MODE

The present invention relates to the development of a carbonic anhydrase that has high stability as well as high activity at a high temperature of 80° C. which is a desorption temperature after capture of carbon dioxide and thus can be mass-produced using an *E. coli* expression system for the purpose of application to a carbon dioxide capture process.

In one embodiment of the present invention, a recombinant *Escherichia coli* expressing KJR78985.1 protein derived from *Sulfolobales archaeon* AZ1 has been constructed, a wild-type carbonic anhydrase derived from *S. archaeon* AZ1 has been produced from the recombinant *Escherichia coli*, and the heat resistance and carbon dioxide capture activity thereof have been determined. Also, active site of the wild-type carbonic anhydrase has been identified and one or more amino acid at the active site have been substituted with another amino acid by site-directed mutagenesis to produce a carbonic anhydrase mutant, and it has been confirmed that the produced carbonic anhydrase mutant has higher carbon dioxide capture activity than the wild-type carbonic anhydrase.

Therefore, in one aspect, the present invention is directed to a carbonic anhydrase mutant including an A58G mutation in an amino acid sequence set forth in SEQ ID NO: 1.

In one embodiment of the present invention, a mutant 1.0 including an A58G mutation in the amino acid sequence of SEQ ID NO: 1 has been produced, and a carbonic anhydrase mutant 13.0 further including a P53G mutation in the mutant 1.0 has been produced.

```
Wild-type carbonic anhydrase amino acid sequence
                                          (SEQ ID NO: 1)
MRVIMSCMDYRLTEEIMKKMDQNTIVLRNAGANVNEFKDILKSLNPDEVV

YLPHTDCAAMKLVLSSVKQGEQVIPKIESSLVSQFRGRQFNDLKELEELN

LKLGLETIKQVVPKAKVISELIDVNKLKWPERKPVVYLLKSTSKYTNEMI

GGYVIQSMNKTSIEADLEIASKLNLKVVKDEFSNARD

Mutant 1.0 amino acid sequence
                                          (SEQ ID NO: 2)
MRVIMSCMDYRLTEEIMKKMDQNTIVLRNAGANVNEFKDILKSLNPDEVV

YLPHTDCGAMKLVLSSVKQGEQVIPKIESSLVSQFRGRQFNDLKELEELN

LKLGLETIKQVVPKAKVISELIDVNKLKWPERKPVVYLLKSTSKYTNEMI

GGYVIQSMNKTSIEADLEIASKLNLKVVKDEFSNARD

Mutant 13.0 amino acid sequence
                                          (SEQ ID NO: 3)
MRVIMSCMDYRLTEEIMKKMDQNTIVLRNAGANVNEFKDILKSLNPDEVV

YLGHTDCGAMKLVLSSVKQGEQVIPKIESSLVSQFRGRQFNDLKELEELN

LKLGLETIKQVVPKAKVISELIDVNKLKWPERKPVVYLLKSTSKYTNEMI

GGYVIQSMNKTSIEADLEIASKLNLKVVKDEFSNARD
```

Both of the enzyme activities of carbonic anhydrase mutants were saturated imidiately at a lower amount of the enzyme than the wild-type carbonic anhydrase, and the mutant 1.0 showed the highest carbon dioxide capture activity.

In another aspect, the present invention is directed to a nucleic acid encoding the carbonic anhydrase mutant, a recombinant vector including the nucleic acid, and a recombinant microorganism introduced with the recombinant vector.

The carbonic anhydrase mutant of the present invention can be mass-produced through recombinant microorganisms. In one embodiment of the present invention, a carbonic anhydrase mutant has been produced using recombinant *E. coli* transformed with a pET vector system into which a nucleic acid encoding the carbonic anhydrase mutant is introduced.

As used herein, the term "vector" means a DNA product containing a DNA sequence operably linked to a control sequence capable of expressing DNA in a suitable host. The vector may be a plasmid, a phage particle or a simple potential genome insert. Once the vector is transformed with an appropriate host, it may replicate and function independently of the genome of the host, or may be integrated with the genome itself. Since the plasmid is the most commonly used type of vector, the terms "plasmid" and "vector" are sometimes used interchangeably throughout the specification of the present invention. However, the present invention includes other forms of vectors having identical functions to those already known or to be known in the art. Typical expression vectors for mammalian cell culture expression are based on, for example, pRK5 (EP 307,247), pSV16B (WO 91/08291) and pVL1392 (Pharmingen).

As used herein, the term "expression control sequence" means a DNA sequence essential for the expression of an operably linked coding sequence in a particular host organism. Such a control sequence includes promoters for conducting transcription, operator sequences for controlling such transcription, sequences for encoding suitable mRNA ribosome-binding sites, and sequences for controlling the termination of transcription and translation. For example, control sequences suitable for prokaryotes include promoters, optional operator sequences and ribosome-binding sites. Eukaryotic cells include promoters, polyadenylation signals and enhancers. The factor that has the greatest impact on the expression level of the gene in the plasmid is a promoter. SRα promoters, cytomegalovirus-derived promoters and the like are preferably used as promoters for high expression.

Any of a wide variety of expression control sequences may be used for the vector in order to express the DNA sequences of the present invention. Useful expression control sequences include, for example, the early and late promoters of SV40 or adenovirus, the lac system, the trp system, the TAC or TRC system, T3 and T7 promoters, the major operator and promoter regions of phage lambda, control regions of fd code proteins, promoters of 3-phosphoglycerate kinase or other glycol lyases, promoters of the phosphatase, such as Pho5, promoters of yeast alpha-mating systems and other sequences having configurations and inductions known to control the expression of genes of prokaryotic or eukaryotic cells or viruses thereof and various combinations thereof. The T7 RNA polymerase promoter Φ10 may be useful for expressing proteins in *E. coli*.

When a nucleic acid sequence is placed together with another nucleic acid sequence based on a functional relationship, it is "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide, when expressed as a pre-protein involved in the secretion of the polypeptide; a promoter or enhancer is operably linked to a coding sequence when it affects the transcription of the sequence; or a ribosome-binding site is operably linked to a coding sequence when it affects the transcription of the sequence; or the ribosome-binding site is operably linked to a coding sequence when positioned to facilitate translation. Generally, "operably linked" means that the linked DNA sequence is in contact therewith, or for a secretory leader, it is in contact therewith and is present in the reading frame.

However, an enhancer need not be in contact therewith. The linkage of these sequences is carried out by ligation (linkage) at convenient restriction enzyme sites. When no such site exists, a synthetic oligonucleotide adapter or a linker according to a conventional method is used.

As used herein, the term "expression vector" commonly refers to a recombinant carrier, into which a fragment of heterologous DNA is inserted, and generally means a fragment of double-stranded DNA. Herein, the heterologous DNA is xenogenous DNA that is not naturally found in the host cell. Once an expression vector is present in a host cell, it can replicate independently of the host chromosomal DNA, and several copies of the vector and inserted (heterologous) DNA thereof can be produced.

As is well known in the art, in order to increase the expression level of a transgene in a host cell, the gene should be operably linked to a transcriptional/translational expression control sequence that functions in a selected expression host. Preferably, the expression control sequence and the corresponding gene are included in one recombinant vector containing both a bacterial selection marker and a replication origin. When the expression host is a eukaryotic cell, the recombinant vector should further include a useful expression marker in the eukaryotic expression host.

A wide variety of expression host/vector combinations can be used to express the DNA sequences of subject proteins of the invention. Suitable expression vectors for eukaryotic hosts include, for example, expression control sequences derived from SV40, cow papillomavirus, adenovirus, adeno-associated virus, cytomegalovirus and retrovirus. Expression vectors that can be used for bacterial hosts include bacterial plasmids that can be exemplified by those obtained from *E. coli*, such as pBlueScript, pGEX2T, pUC vectors, col E1, pCR1, pBR322, pMB9 and derivatives thereof, plasmids having a wide host range such as RP4, phage DNA that can be exemplified by a wide variety of phage lambda derivatives such as λgt10, λgt11 and NM989, and other DNA phages such as M13 and filamentous single-stranded DNA phages. Expression vectors useful for yeast cells include 2μ plasmids and derivatives thereof. The vector useful for insect cells is pVL 941.

The host cell transfected or transformed with the recombinant vector described above constitutes another aspect of the present invention. As used herein, the term "transfection" means introducing DNA into a host and making the DNA replicable by an extrachromosomal factor or chromosomal integration. As used herein, the term "transformation" means that an expression vector is accommodated by the host cell, regardless of whether or not any coding sequence is actually expressed.

The host cell of the invention may be a prokaryotic or eukaryotic cell. In addition, a host having high introduction efficiency of DNA and high expression efficiency of the introduced DNA is usually used. Examples of the host cell that can be used include well-known eukaryotic and prokaryotic hosts such as *E. coli, Pseudomonas, Bacillus, Streptomyces*, fungi and yeast, insect cells such as *Spodoptera frugiperda* (SF9), animal cells such as CHO and mouse cells, African green monkey cells such as COS 1, COS 7, BSC 1, BSC 40 and BMT 10, and tissue-cultured human cells. When the cDNA encoding the protein of the present invention is cloned, it is preferable to use an bacterial cell as a host. In the present invention, *E. coli* is exemplified, but the present invention is not limited thereto. When COS cells are used, SV40 large T antigen is expressed in the COS cells. Therefore, the plasmid having a replication origin of SV40 is present as multiple episome copies in the cells, so that higher expression can be expected. The introduced DNA sequence may be obtained from the same species as the host cell, may be a different species from the host cell, or may be a hybrid DNA sequence including any heterologous or homologous DNA.

It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of replications of the vector, the ability to control the number of replications, and the expression of other proteins encoded by the corresponding vector, such as the expression of antibiotic markers, should also be considered. In selecting the expression control sequence, a number of factors should be considered. For example, the relative strength of the sequence, controllability, and compatibility with the DNA sequences of the present invention should be considered, particularly in relation to possible secondary structures. The single-cell host may be selected in consideration of factors such as the selected vector, the toxicity of the product encoded by the DNA sequence of the present invention, secretion characteristics, the ability to accurately fold proteins, culture and fermentation factors, and ease of purification of the product encoded by the DNA sequence according to the present invention. Within the scope of these factors, those skilled in the art can select various vector/expression control sequences/host combinations capable of expressing the DNA sequences of the present invention in fermentation or large cultures. As a screening method for cloning cDNA of proteins through expression cloning, a binding method, a panning method, a film emulsion method or the like can be applied.

In another aspect, the present invention is directed to a method for producing a carbonic anhydrase mutant comprising: (a) culturing the recombinant microorganism to produce a carbonic anhydrase mutant; and (b) recovering the produced carbonic anhydrase mutant.

In another aspect, the present invention is directed to a composition for capturing carbon dioxide containing the carbonic anhydrase mutant and a method for capturing carbon dioxide at 40 to 90° C. using the carbonic anhydrase mutant.

The composition for capturing carbon dioxide may include the carbonic anhydrase mutant, a recombinant microorganism transformed with a nucleic acid encoding the enzyme mutant, a lysate of the microorganism, or an extract of the microorganism lysate.

The heat-resistant carbonic anhydrase mutant according to the present invention has high stability as well as excellent activity at a high temperature of 80° C., which is a desorption temperature after capture of carbon dioxide and can be mass-produced using an *E. coli* expression system, thus being applicable to a carbon dioxide capture process.

Hereinafter, the present invention will be described in more detail with reference to the following examples. However, it will be obvious to those skilled in the art that the following examples are provided only for illustration of the present invention and should not be construed as limiting the scope of the present invention.

Example 1

Construction of Recombinant *Escherichia coli* Producing Wild-Type Carbonic Anhydrase Based on the genomic information of the NCBI database, a codon-optimized nucleic acid was synthesized so as to express a nucleic acid encoding the KJR78985.1 protein, which is a carbonic anhydrase derived from *Sulfolobales archaeon* AZ1, in *Escherichia coli*, and then inserted into a pUCIDT-AMP vector (Integrated DNA Technologies, USA). The nucleic acid encoding the carbonic anhydrase gene was introduced into the pET-28b(+) vector (Novagen, USA) using an NdeI/XhoI restriction enzyme to produce a recombinant expression vector. The carbonic anhydrase gene in the pET-28b(+) vector had a histidine tag capable of binding Ni ions at the C-terminus. The recombinant vector was introduced into the host cell, *E. coli* BL21 (DE3), by a thermal-shock method at 42° C. for 45 seconds, and *Escherichia coli* introduced with the recombinant vector was selected in LB medium supplemented with kanamycin to produce a recombinant *Escherichia coli* transformed with a carbonic anhydrase gene.

Example 2

Expression and Purification of Wild-Type Carbonic Anhydrase

The recombinant *E. coli* transformed with the wild-type carbonic anhydrase gene prepared in Example 1 was inoculated into 100 ml of LB (+Kan) medium, cultured at 37° C. for 18 hours, and added with 1 mM IPTG at OD of 0.4 to 0.6, followed by further incubation at 37° C. for 5 hours to express carbonic anhydrase. The cultured solution was collected and the cells were recovered by centrifugation at 4° C. and 4500 rpm, washed with 50 mM PBS buffer (pH 7.0), suspended in 30 ml of binding buffer, and sonicated (sonication conditions: pulse 2 seconds on/10 seconds off 12 minutes, 50% amplitude). The resulting solution was centrifuged at 12,000 rpm at 4° C. for 20 minutes to recover the supernatant, and the protein was purified using a Ni-NTA column. The eluate was centrifuged at 4,000 g for 30 minutes in an ultracentrifuge (Amicon ultra), and the buffer was changed to 15 ml of 20 mM Tris-HCl (pH 8.0) buffer. The obtained wild-type carbonic anhydrase was protein-assayed by a BCA method, and 300 µl of a purified enzyme was obtained at a concentration of 9.3 mg/ml.

The buffer system used for enzyme purification is as follows.

Binding buffer: 20 mM Tris-HCl, 300 mM NaCl, 20 mM imidazole, (pH 8.0)

Wash buffer: 20 mM Tris-HCl, 300 mM NaCl, 50 mM imidazole, (pH 8.0)

Elution buffer: 20 mM Tris-HCl, 300 mM NaCl, 250 mM imidazole, (pH 8.0)

For buffer change: 20 mM Tris-HCl, 300 mM NaCl (pH 8.0)

Figure 1:
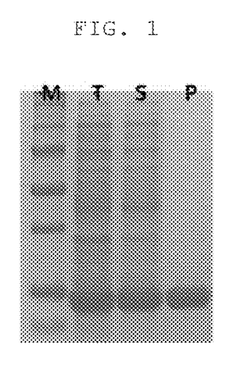
FIG. 1 shows the results of SDS-PAGE analysis of cell lysate and purified protein after expression of a wild-type carbonic anhydrase in the cytoplasm.

FIG. 1 shows the results of SDS-PAGE analysis of the carbonic anhydrase expression before and after purification. The carbonic anhydrase was successfully expressed in the cytoplasm of *E. coli*, and the purification rate and purity were high. M represents a molecular weight standard marker, T represents the whole cell lysate, S represents a cell lysis supernatant, and P represents a purified carbonic anhydrase protein.

Example 3

Figure 2:
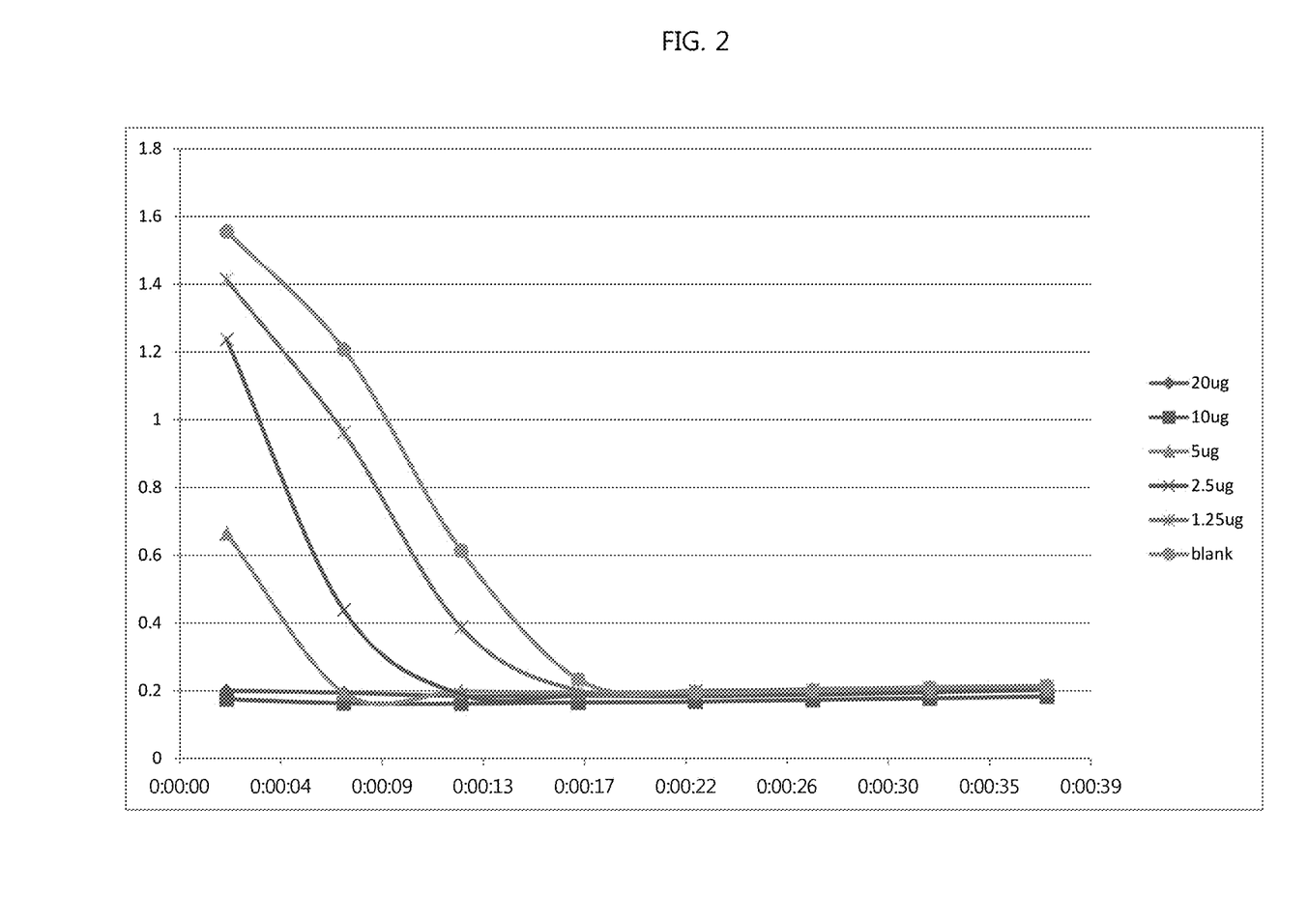
FIG. 2 shows the results of measurement of carbon dioxide capture activity of the purified wild-type carbonic anhydrase at different concentrations.

Identification of Carbon Dioxide Capture Activity of Wild-Type Carbonic Anhydrase The carbon dioxide capture activity was measured using the wild-type carbonic anhydrase obtained in Example 2. Primarily distilled water and carbonic acid were sequentially injected into a carbonated water production bottle and the bottle was allowed to stand for 2 hours in a water tank filled with ice. 120 µl of buffer (20 mM Tris-sulfate, pH 8.3), 30 µl of 0.04% BTB Solution (Sigma-Aldrich), 40 µl of distilled water and 10 µl of carbonic anhydrase solution were added to a 96-well plate, and then 50 µl of carbonic acid water was added thereto. The absorbance was measured at 610 nm for 2 minutes. The enzyme was added at different concentrations of 20 µg, 10 µg, 5 µg, 2.5 µg, 1.25 µg and 0.625 µg to the reaction mixture. As a result, as can be seen from FIG. 2, the reaction rate with the carbonic acid water was slow upon addition of 5 µg of the enzyme. The blank was a control group containing no carbonic anhydrase. The pH of the experimental group, to which the carbonic anhydrase was added, was lowered faster than that of the control group with nothing added thereto, which means that the carbonic anhydrase has high activity for capturing carbon dioxide.

Example 4

Heat Resistance and Stability of Wild-Type Carbonic Anhydrase

In order to identify the heat resistance and stability of the wild-type carbonic anhydrase, while the carbonic anhydrase obtained in Example 2 was stored at 80° C., the degree of decrease in carbon dioxide capture activity was periodically measured. The same activity measurement method used in Example 3 was used.

As can be seen from Table 1, the results showed that the value of $t_{1/2}$ at which the enzyme activity was halved was 20 days, and that the carbonic anhydrase enzyme according to the present invention was more heat resistant and stable than carbonic anhydrase enzymes reported to date.

TABLE 1

Comparison of heat resistance and stability between the wild-type carbonic anhydrase and previously reported carbonic anhydrases

| Carbonic anhydrase | TaCA | mDvCA | SspCA | SazCA | PmCA | CA of present invention |
|---|---|---|---|---|---|---|
| Heat stability ($t_{1/2}$, day) | 77 days (60° C.) | 42 days (60° C.) | 8 days (70° C.) | 8 days (70° C.) | 3.6 hr (90° C.) 1.46 hr (100° C.) | 20 days (80° C.) |

Reference: Anna Di Fiore et. al. Thermostable Carbonic Anhydrases in Biotechnological Applications; Int. J. Mol. Sci. 2015 Jul. 8; 16(7):15456-80

Example 5

Production of Carbonic Anhydrase Mutants

In order to improve the carbon dioxide capture activity of the heat-resistant wild-type carbonic anhydrase derived from *Sulfolobales archaeon* AZ1 obtained in Example 3, the active site of the enzyme was analyzed. The results indicated that the carbonic anhydrase belongs to a beta-type carbonic anhydrase and has alanine, instead of glycine, in the active site of the amino acid at position 58. Thus, a carbonic anhydrase mutant 1.0 was produced by substituting alanine at position 58 with glycine. In addition, a carbonic anhydrase mutant 13.0 was produced by substituting proline at position 53, presumed to be the active site, with glycine, in addition to the substitution with glycine at position 58. (see Table 2).

The mutants were prepared through PCR using the QuikChange II Site-Directed Mutagenesis Kit (Agilent, USA) and the mutated amino acid information and the primers that were used are shown in Table 2 and Table 3.

TABLE 2

Mutation positions and information of carbonic anhydrase mutants

| Carbonic anhydrase | | |
|---|---|---|
| Position | 58 | 53 |
| wild type | A | P |
| 1.0 | G | G |
| 13.0 | GG | G | G |

TABLE 3

Primers and templates used for mutations

| | Template | Sequence -F | Sequence -R |
|---|---|---|---|
| 1.0 | Wild type | 5'-CAC ACC GAC TGC GGC GCG ATG AAA CTG-3' (SEQ ID NO: 4) | 5'-CAG TTT CAT CGC GCC GCA GTC GGT GTG-3' (SEQ ID NO: 5) |
| 13.0 | Mutant 1.0 | 5'-GTTGTGTACCTGGGCCACACCGAC TG-3' (SEQ ID NO: 6) | 5'-CAGTCGGTGTGGCCCAGGTACACAAC-3' (SEQ ID NO: 7) |

*E. coli* BL21 (DE3) was transformed with a vector, into which the produced mutant gene was inserted, by a thermal-shock method at 42° C. for 45 seconds, and the transformed *E. coli* introduced with the vector was selected in LB medium supplemented with kanamycin to produce recombinant *E. coli*.

Example 6

Expression and Purification of Carbonic Anhydrase Mutants

Figure 3:
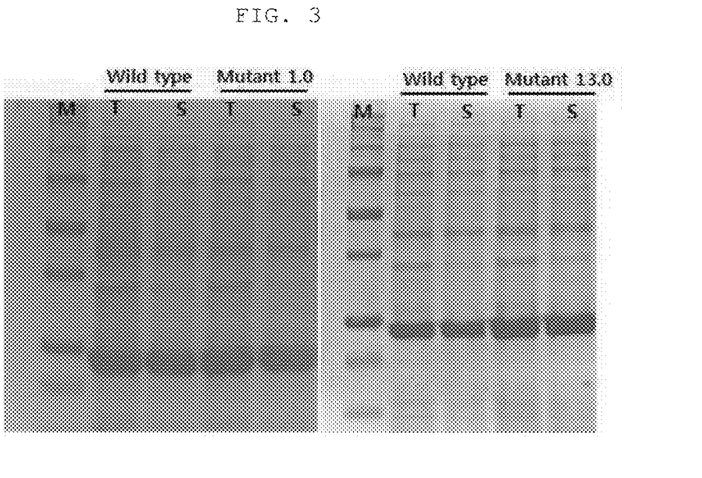
FIG. 3 shows the results of SDS-PAGE analysis of cell lysate and purified protein after expression of the carbonic anhydrase mutant in the cytoplasm.
Figure 4:
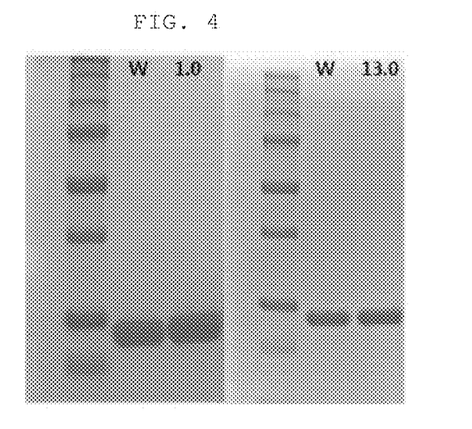
FIG. 4 shows the results of SDS-PAGE analysis of the purified carbonic anhydrase mutant.

The carbonic anhydrase mutants were expressed in *E. coli* and purified in the same manner as in Example 2. As shown in FIGS. 3 and 4, the results of SDS-PAGE analysis showed the mutants were successfully expressed in the cytoplasm of recombinant *E. coli* and that the purification rate and purity were high. M represents a molecular weight standard marker, T represents the whole cell lysate, and S represents a cell lysate supernatant.

Example 7

Figure 5:
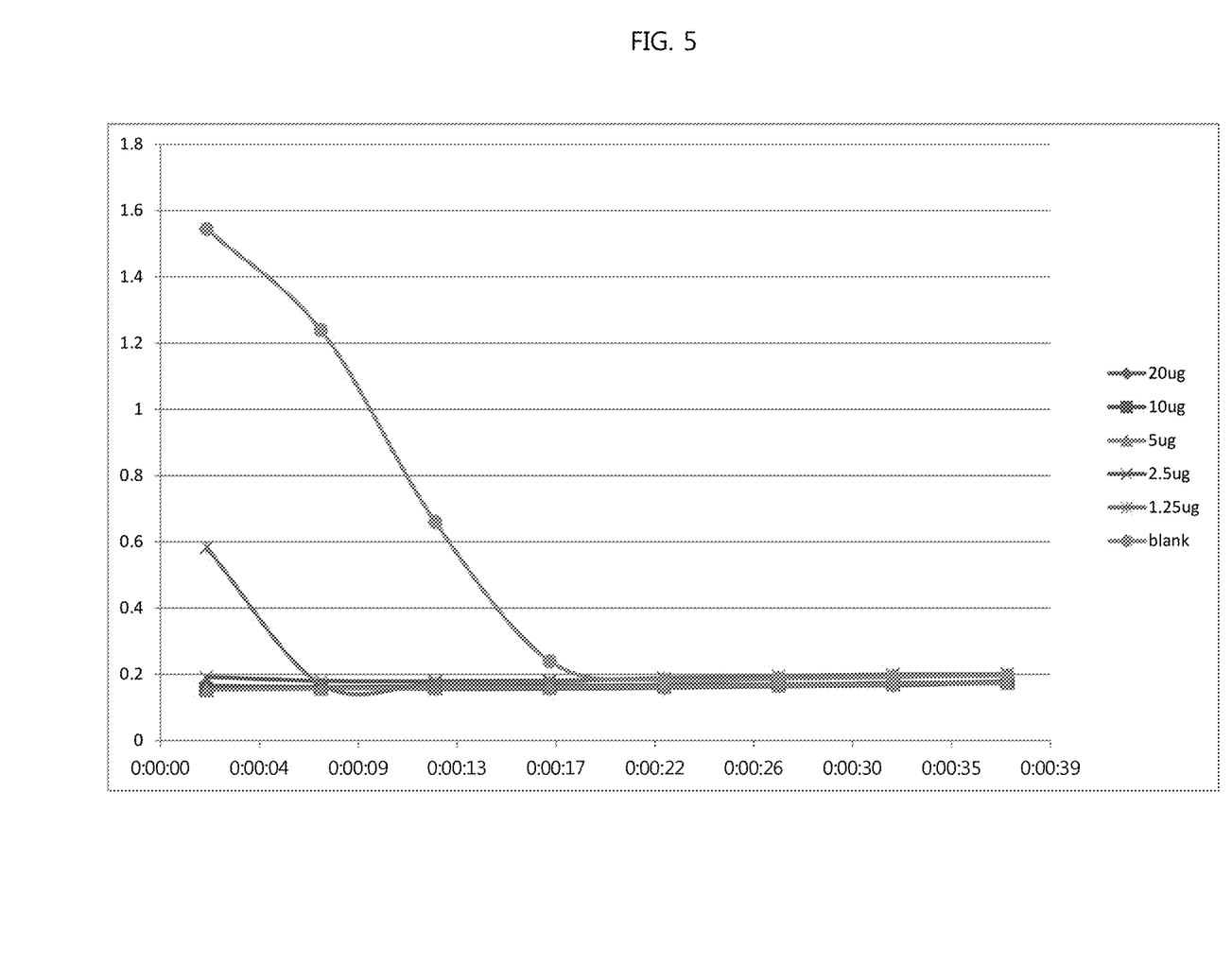
FIG. 5 shows the results of measurement of the carbon dioxide capture activity of purified carbonic anhydrase mutant 1.0 at different concentrations.
Figure 6:
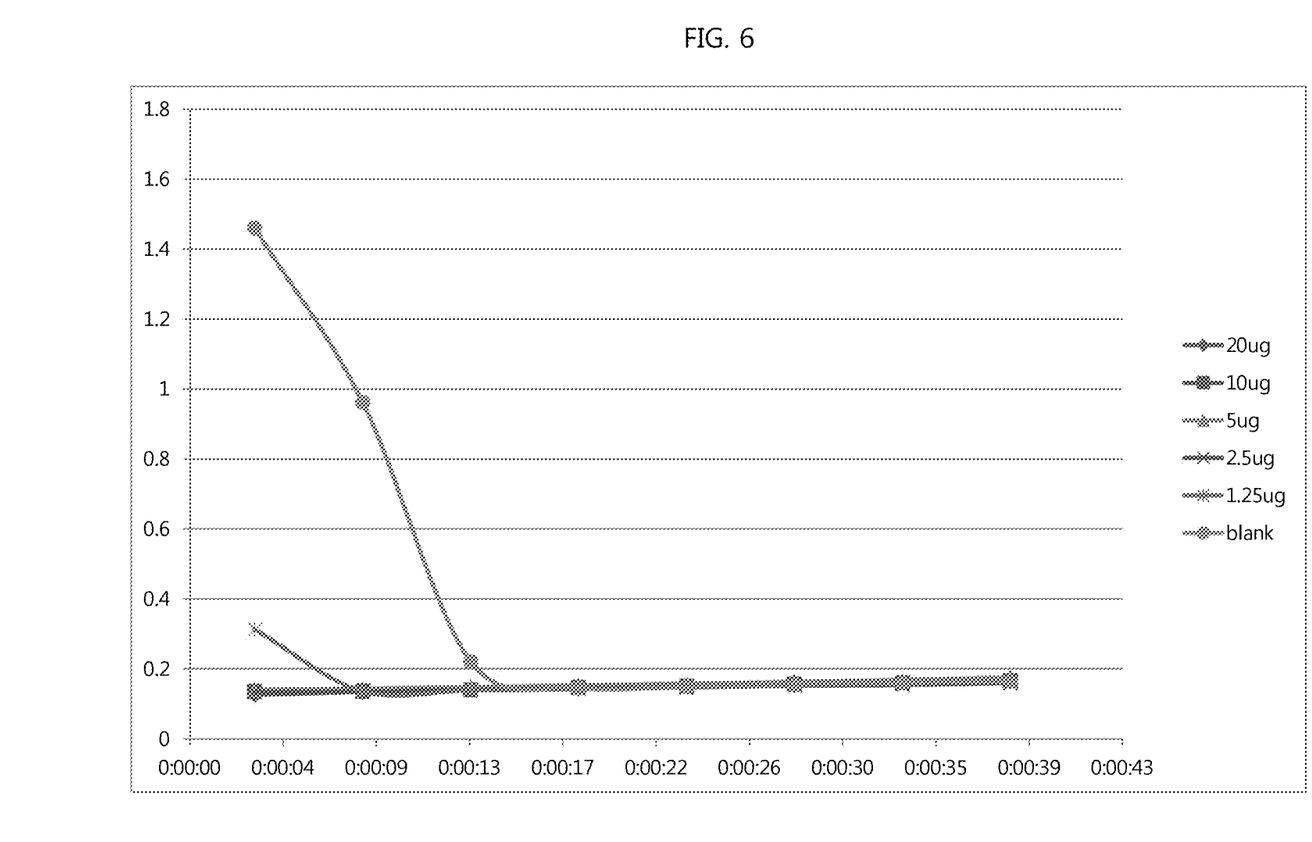
FIG. 6 shows the results of measurement of the carbon dioxide capture activity of purified carbonic anhydrase mutant 13.0 at different concentrations.

Identification of Carbon Dioxide Capture Activity of Carbonic Anhydrase Mutants The carbon dioxide capture activity of the carbonic anhydrase mutants obtained in Example 6 was measured. Primarily distilled water and carbonic acid were sequentially injected into a carbonated water production bottle and the bottle was allowed to stand for 2 hours in a water tank filled with ice. 120 μl of buffer (20 mM Tris-sulfate, pH 8.3), 30 μl of a 0.04% BTB Solution, 40 μl of distilled water and 10 μl of an enzyme were added to a 96-well plate, and then 50 μl of carbonic acid water was added thereto. The absorbance was measured at 610 nm for 2 minutes. The enzyme was added at different concentrations of 20 μg, 10 μg, 5 μg, 2.5 μg, and 1.25 μg to the reaction mixture, the measurement was conducted at each concentration, and the results for the mutants are shown in FIG. 5. Table 4 summarizes the enzyme activity. Both enzyme mutants had smaller amounts of the enzyme that saturates the initial reaction rate than the wild-type enzyme, and mutant 1.0 showed the highest carbon dioxide capture activity.

TABLE 4

Comparison of carbon dioxide capture activity between wild-type carbonic anhydrase and carbonic anhydrase mutants

| | Wild type | Mutant 1.0 | Mutant 13.0 |
|---|---|---|---|
| Amount of enzyme saturating initial reaction rate [μg] | 10 | 2.5 | 2.5 |

TABLE 4-continued

Comparison of carbon dioxide capture activity between wild-type carbonic anhydrase and carbonic anhydrase mutants

| | Wild type | Mutant 1.0 | Mutant 13.0 |
|---|---|---|---|
| Increase in activity compared to wild type [times] | — | 4 | 4 |

Example 8

Heat Resistance and Stability of Carbonic Anhydrase Mutant

In order to compare the heat resistance and stability between the carbonic anhydrase mutant and wild-type carbonic anhydrase, while the carbonic anhydrase mutant obtained in Example 6 was stored at 80° C., the degree of decrease in carbon dioxide capture activity was periodically measured. The same activity measurement method used in Example 3 was used.

As can be seen from Table 5, the results showed that the mutant 1.0 exhibited a 31% increase in heat resistance and the mutant 13.0 exhibited a 21% increase in heat resistance compared to the wild-type carbonic anhydrase.

TABLE 5

Comparison in heat resistance and stability between carbonic anhydrase mutants and wild-type carbonic anhydrase

| Carbonic anhydrase | Wild-type | Mutant 1.0 | Mutant 13.0 |
|---|---|---|---|
| Increase in heat stability [%] | 100 | 131 | 121 |

Although the specific configurations of the present invention have been described in detail, those skilled in the art will appreciate that this description is provided as preferred embodiments and should not be construed as limiting the scope of the present invention. Therefore, the substantial scope of the present invention is defined by the accompanying filed claims and equivalents thereto.

The invention claimed is:

1. A carbonic anhydrase mutant comprising an A58G mutation in the amino acid sequence set forth in SEQ ID NO: 1.

2. The carbonic anhydrase mutant according to claim 1, further comprising a P53G mutation.

3. A nucleic acid encoding the carbonic anhydrase mutant according to claim 1.

4. A recombinant vector comprising the nucleic acid according to claim 3.

5. A recombinant microorganism comprising the nucleic acid according to claim 3.

6. A recombinant microorganism comprising the recombinant vector according to claim 4.

7. A method for producing a carbonic anhydrase mutant comprising:
   (a) culturing the recombinant microorganism according to claim 5 to produce a carbonic anhydrase mutant; and
   (b) recovering the produced carbonic anhydrase mutant.

8. A method for producing a carbonic anhydrase mutant comprising:
   (a) culturing the recombinant microorganism according to claim 6 to produce a carbonic anhydrase mutant; and
   (b) recovering the produced carbonic anhydrase mutant.

9. A composition for capturing carbon dioxide comprising the carbonic anhydrase mutant according to claim 1.

10. A composition for capturing carbon dioxide comprising the carbonic anhydrase mutant according to claim 2.

11. A method for capturing carbon dioxide at 40 to 90° C. comprising contacting the carbonic anhydrase mutant according to claim 1 with a composition or substance comprising said carbon dioxide.

12. A method for capturing carbon dioxide at 40 to 90° C. comprising contacting the carbonic anhydrase mutant according to claim 2 with a composition or substance comprising said carbon dioxide.

* * * * *